(12) United States Patent
McGuckin, Jr. et al.

(10) Patent No.: US 6,589,214 B2
(45) Date of Patent: Jul. 8, 2003

(54) VASCULAR INTRODUCER SHEATH WITH RETAINER

(75) Inventors: James F. McGuckin, Jr., Radnor, PA (US); Paul Tashjian, King of Prussia, PA (US)

(73) Assignee: Rex Medical, L.P., Conshohocken, PA (US)

(*) Notice: Subject to any disclaimer, the term of this patent is extended or adjusted under 35 U.S.C. 154(b) by 0 days.

(21) Appl. No.: 09/995,893

(22) Filed: Nov. 28, 2001

(65) Prior Publication Data

US 2002/0068898 A1 Jun. 6, 2002

Related U.S. Application Data

(60) Provisional application No. 60/251,559, filed on Dec. 6, 2000.

(51) Int. Cl.[7] .................. A61M 5/178; A61M 5/32; A61M 29/00
(52) U.S. Cl. .................. 604/175; 604/165.03; 606/191; 606/198
(58) Field of Search .................. 606/200, 191, 606/198; 604/104, 174, 167.01, 164.12, 105, 523, 500, 108, 117, 177, 191

(56) References Cited

U.S. PATENT DOCUMENTS

| | | |
|---|---|---|
| 4,043,346 A | 8/1977 | Mobley et al. |
| 4,995,868 A | 2/1991 | Brazier |
| 5,273,529 A | 12/1993 | Idowu |
| 5,352,198 A | 10/1994 | Goldenberg et al. |
| 5,437,644 A | 8/1995 | Nobles |
| 5,509,900 A * | 4/1996 | Kirkman ............ 604/104 |
| 5,702,365 A | 12/1997 | King |
| 5,713,870 A | 2/1998 | Yoon |
| 5,716,325 A * | 2/1998 | Bonutti ............ 15/230.19 |
| 5,769,821 A | 6/1998 | Abrahamson et al. |
| 5,817,062 A | 10/1998 | Flom et al. |
| 5,840,067 A | 11/1998 | Berguer et al. |
| 5,857,999 A * | 1/1999 | Quick et al. ............ 604/104 |
| 5,882,340 A * | 3/1999 | Yoon ............ 604/104 |
| 5,971,960 A | 10/1999 | Flom et al. |
| 5,976,172 A * | 11/1999 | Homsma et al. ............ 604/104 |
| 6,071,263 A | 6/2000 | Kirkman |
| 6,187,000 B1 | 2/2001 | Davison et al. |

* cited by examiner

Primary Examiner—Michael J. Hayes
Assistant Examiner—Roz Ghafoorian
(74) Attorney, Agent, or Firm—Neil D Gershon

(57) ABSTRACT

A surgical vascular introducer sheath comprising first and second members and a retainer. The first member has a lumen for receiving a surgical instrument therethrough and a first side opening in an outer wall in fluid communication with the first lumen. The second member has a lumen and a side opening in fluid communication with the second lumen, wherein at least a portion of the first member is positioned within the second lumen of the second member. The retainer is positioned at a distal portion of the first member and is movable from a first retracted position to a second extended position to limit proximal movement of the introducer in response to movement of the first member.

16 Claims, 6 Drawing Sheets

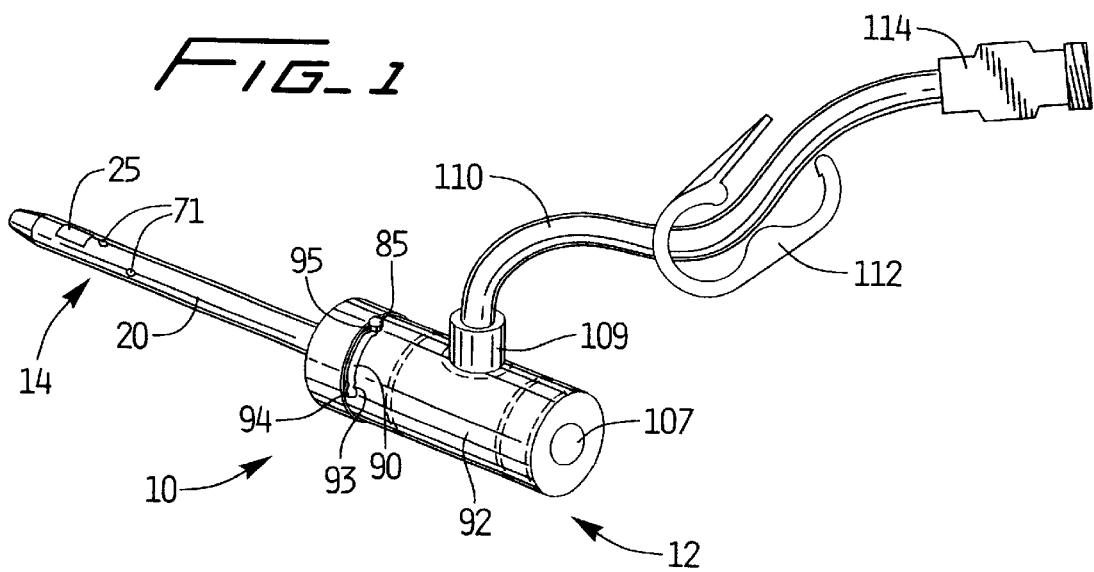
FIG_1
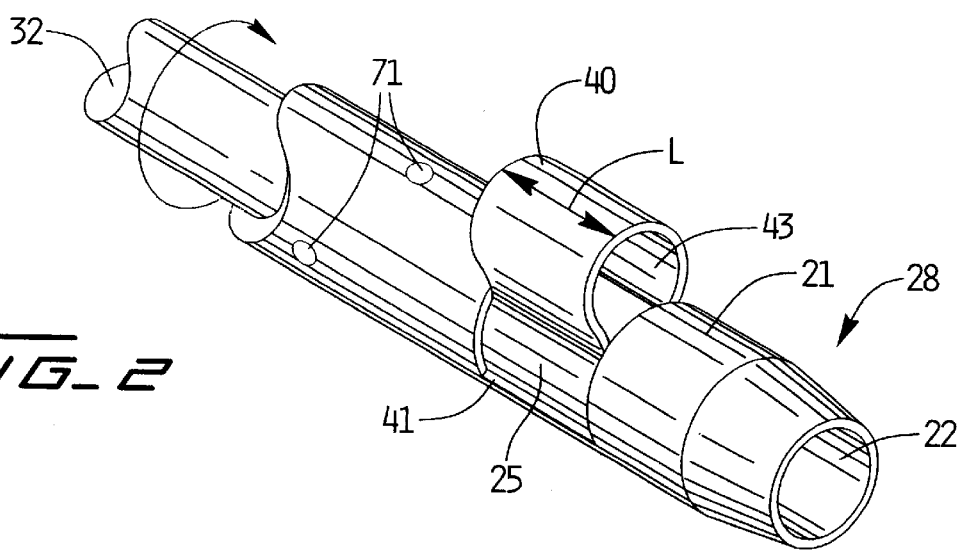
FIG_2
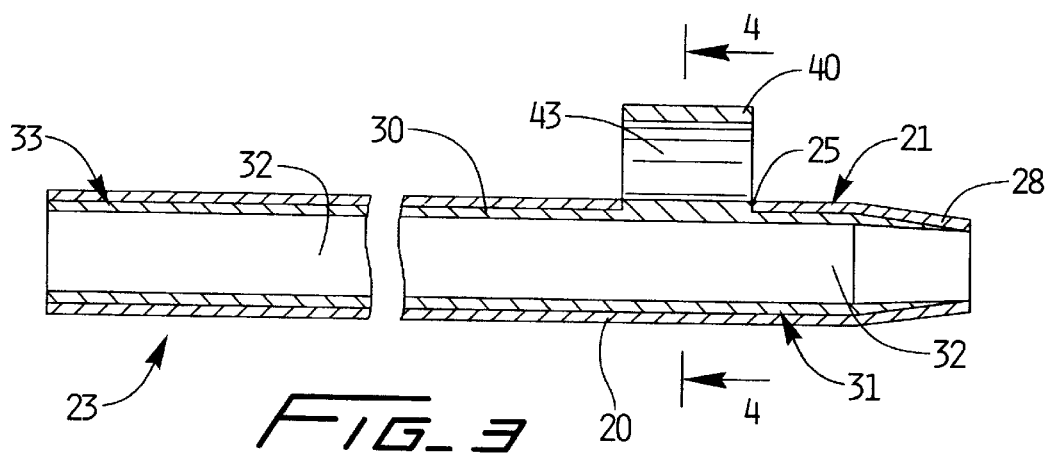
FIG_3

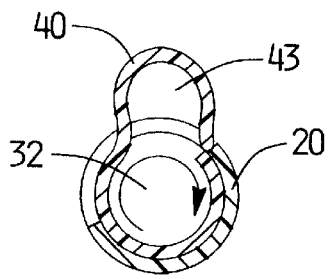
FIG_4
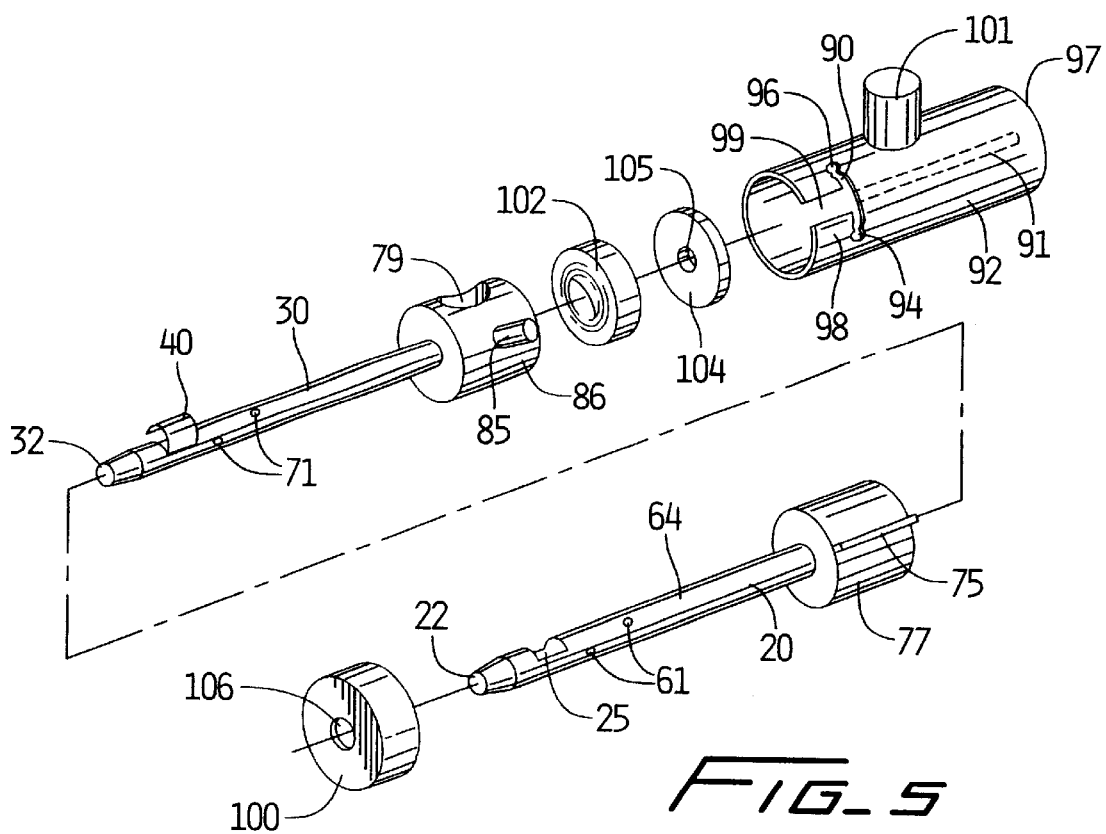
FIG_5
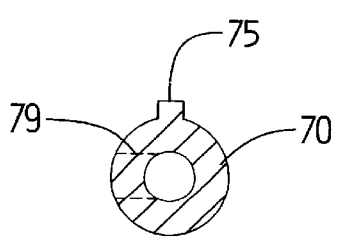
FIG_6
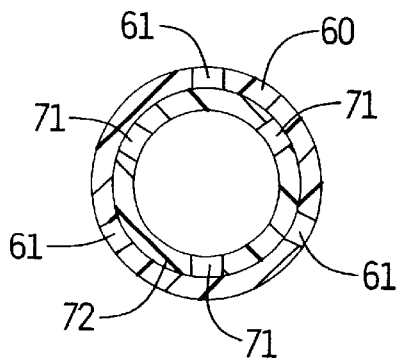
FIG_7

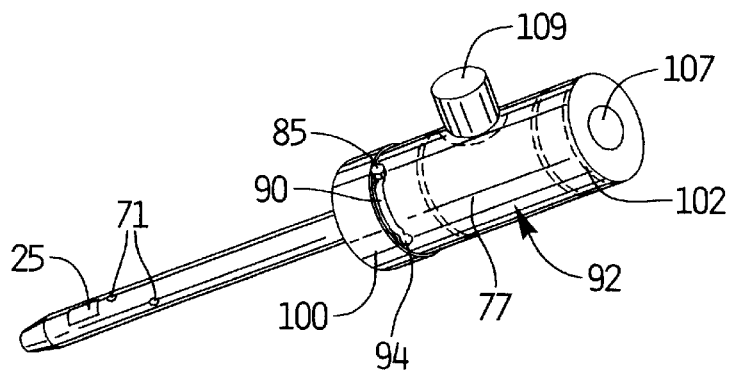
FIG_8
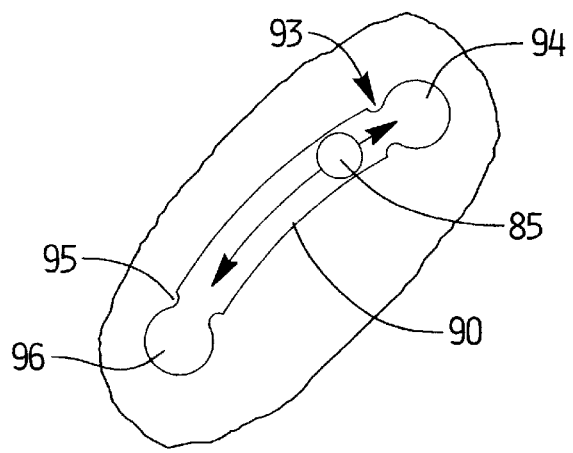
FIG_9
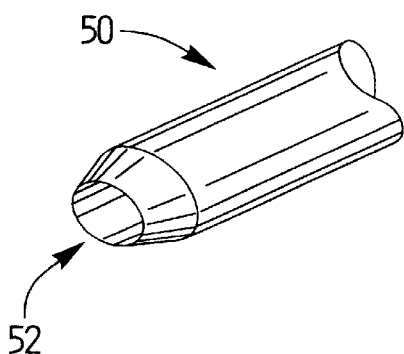
FIG_10
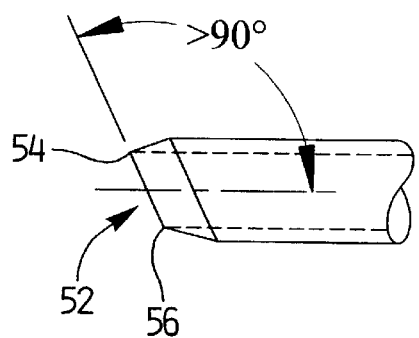
FIG_11

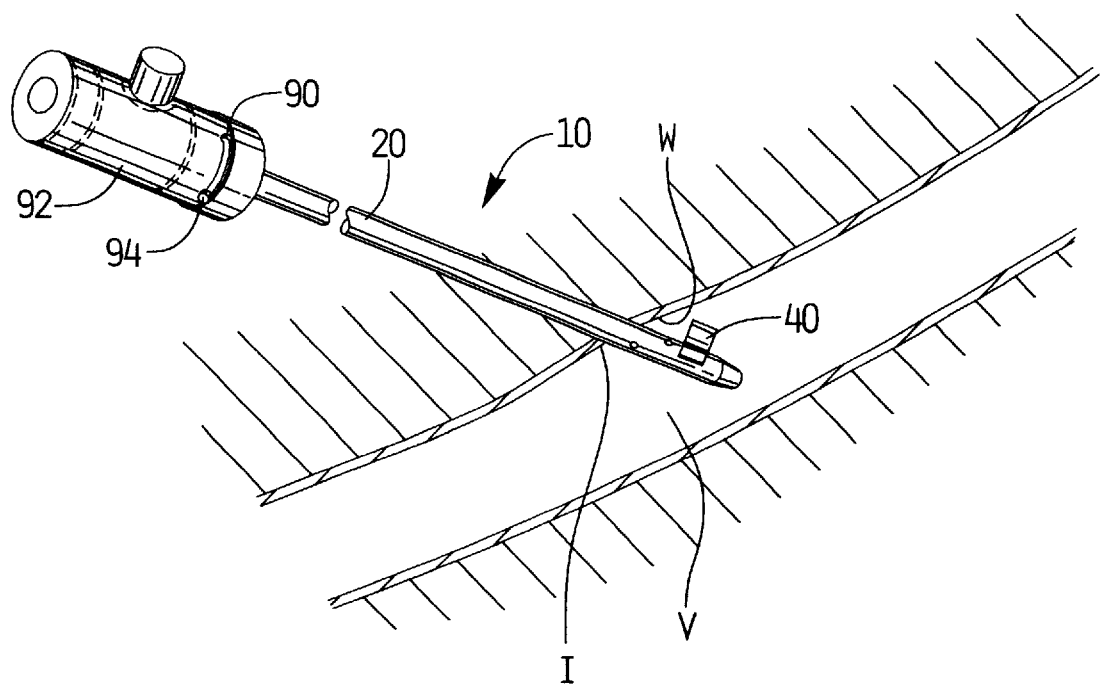
FIG_12
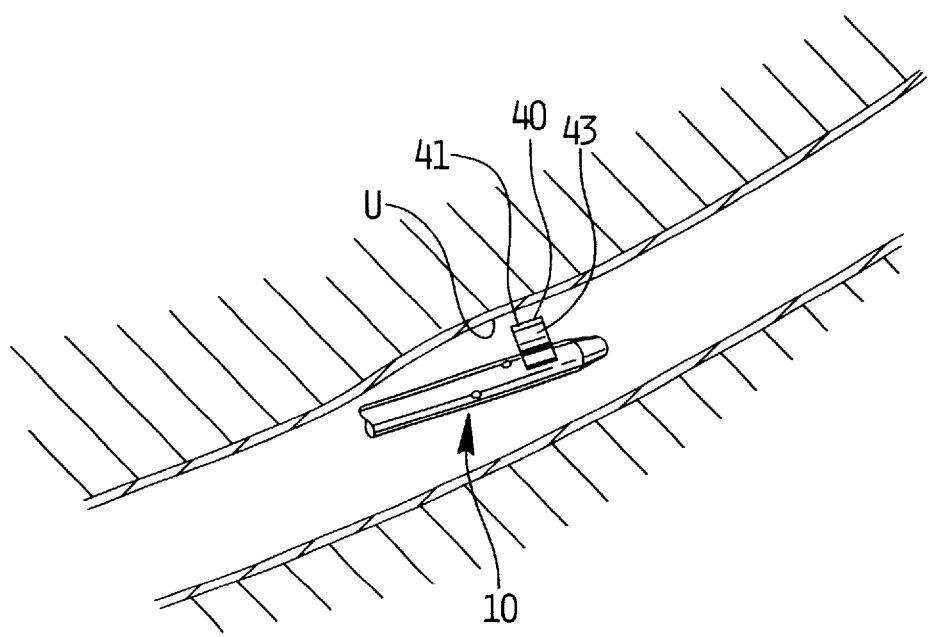
FIG_13

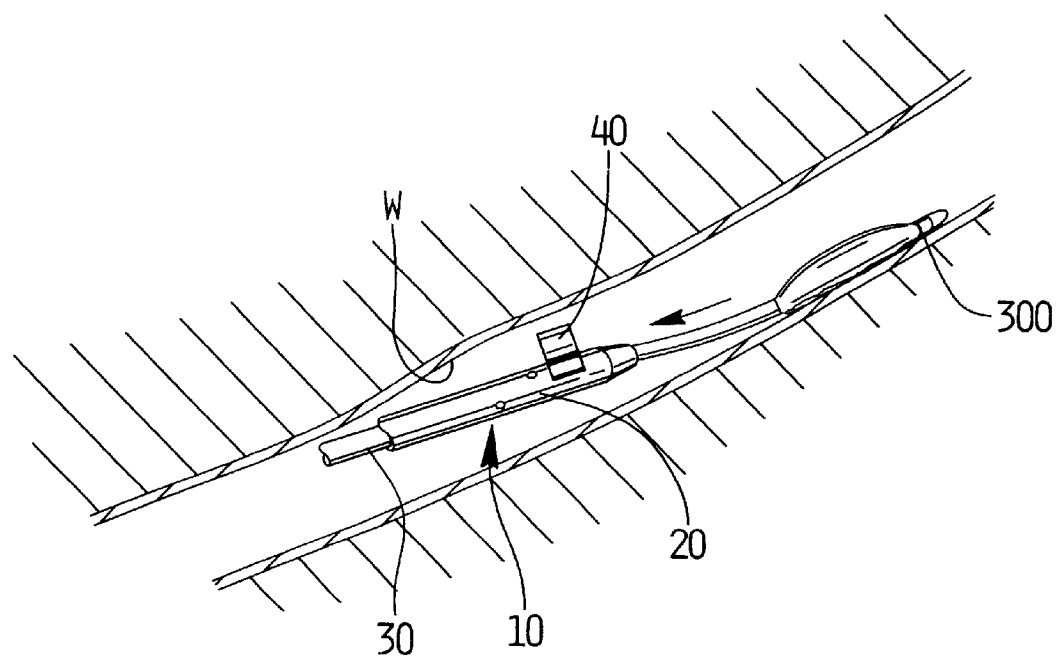
FIG_14
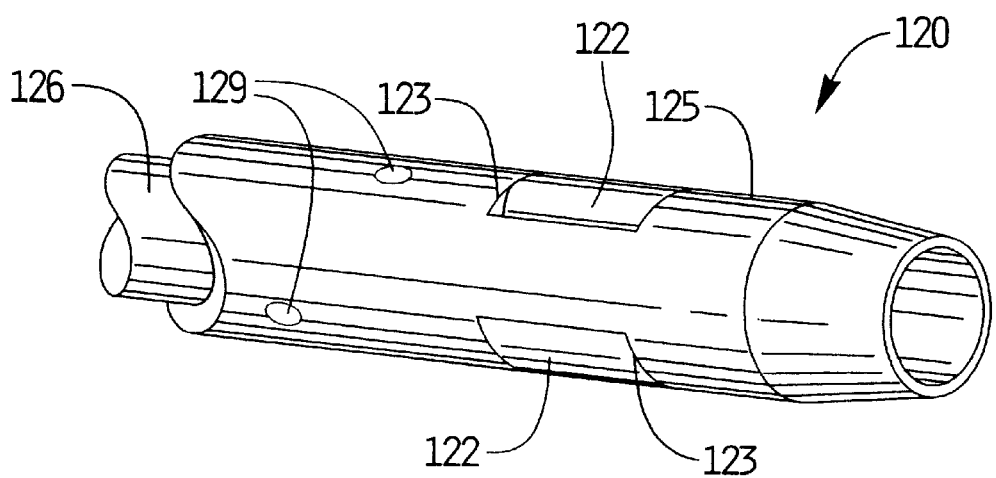
FIG_15

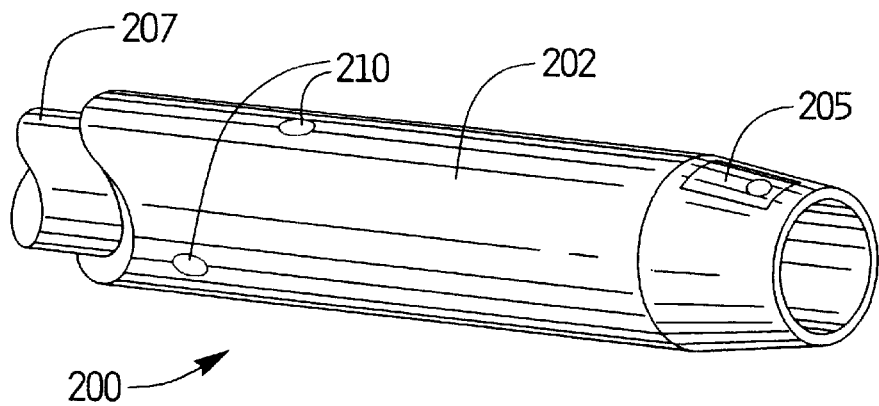
FIG_16
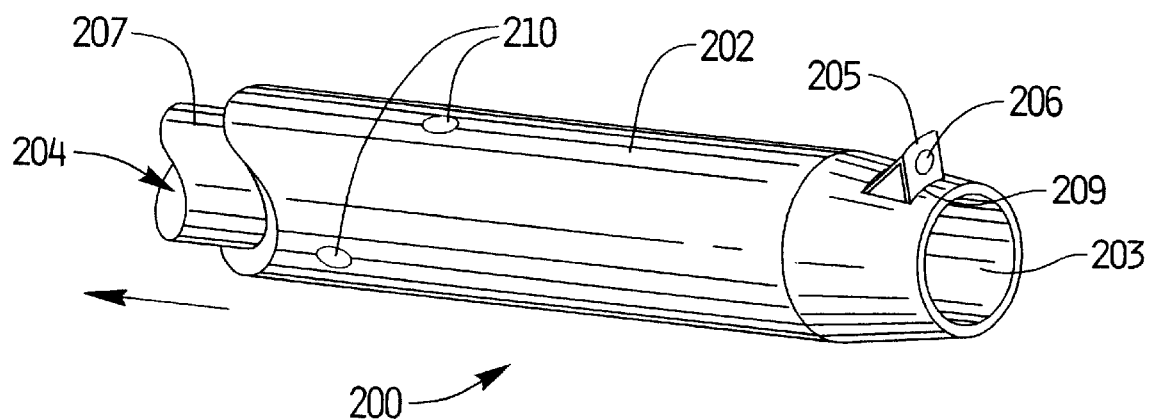
FIG_17

VASCULAR INTRODUCER SHEATH WITH RETAINER

This application claims priority from provisional patent application Ser. No. 60/251,559, filed Dec. 6, 2000, the entire contents of which are incorporated herein by reference.

BACKGROUND

1. Technical Field

This application relates to an introducer sheath and more particularly to a vascular introducer sheath having a retainer to prevent dislodgement during use.

2. Background of Related Art

An introducer sheath is commonly used in vascular surgery as an access port for surgical instruments. The introducer sheath has a central passageway to accommodate such instrumentation and is inserted through a skin incision and into the vessel wall, such as the renal or femoral artery or vein, so the instruments can access the interior of the vessel. The introducer sheath can also be inserted into dialysis grafts to provide access to the graft. The introducer sheaths have peripheral, cardiac, and neurovascular applications.

Once the surgical introducer sheath is placed, various instruments are inserted and withdrawn through the passageway into the vessel interior, depending on the surgical procedure. Examples of such instrumentation include dilators, angioplasty balloon catheters, stent deployment catheters, angiographic instruments, thrombectomy devices and embolization instruments. These instruments typically having an outer diameter close to the internal diameter of the introducer sheath which means they will usually abut the inside wall of the sheath. This relatively tight fit oftentimes results in excessive frictional engagement with the inside wall of the sheath, causing dislodgement of the sheath during instrument withdrawal through the passageway in the sheath. Additionally, surgical instrumentation which include an inflatable balloon, when initially inserted through the sheath have a smaller diameter because the balloon is tightly wrapped around the catheter. However, after the balloon is inflated inside the vessel and then deflated for withdrawal, it is not as tightly wrapped as initial insertion. Thus, when the balloon catheter is withdrawn through the introducer sheath, there is a greater frictional contact with the inside wall of the sheath and therefore a greater likelihood of dislodgement.

Dislodgement of the sheath creates numerous problems. If the position of the sheath is altered by removal of an instrument, when the next instrument is inserted, it will not properly be positioned at the surgical site. Thus the surgeon must undertake the time consuming task of repositioning the sheath and instrument within the vessel. The problems with dislodgement become more acute if withdrawal of the instrument actually pulls the introducer sheath out of the vessel wall incision altogether. This can occur if there is sufficient frictional contact with the instrument and introducer sheath, and a sufficient proximal force is applied by the surgeon. Such undesirable removal of the introducer sheath can cause loss of blood, air aspiration which can result in air embolisms possibly causing stroke, and an increased risk of infection and morbidity. Additionally, since the surgeon needs to reintroduce the introducer sheath into the vessel, the surgeon may be unable to locate the exact prior incision site, thereby having to enlarge the incision site or create a second incision, thereby causing additional blood loss and increasing the difficulty of closing the vessel incision(s) at the end of the procedure. Vessel fatigue can also result because re-introduction of the sheath requires insertion of a needle and dilator through the vessel wall.

Another disadvantage of complete dislodgement of the sheath is the additional time required to re-introduce the sheath. This time loss can be especially significant if re-introduction is required at a critical time of the procedure. That is, if the sheath is fully withdrawn from the vessel, access to the vessel will be temporarily denied, thereby interrupting the surgical procedure which can mean appropriate instrumentation, perhaps even life-saving instrumentation, cannot be inserted to the surgical site.

Due to the concern of dislodgement, surgeons sometimes over-insert the introducer sheath so the tip is spaced further from the incision. This way, if the sheath is inadvertently pulled proximally, it will have some room to move before it is pulled out fully from the incision. However, over-insertion of the introducer sheath can adversely affect surgical access as the surgical site can be blocked by the sheath, especially if the site is adjacent the incision.

Therefore, it would be advantageous to provide a mechanism to retain the introducer sheath within the vessel. However, such mechanism needs to be configured so as not to damage the vessel wall. Consequently, a retaining mechanism must effectively strike a balance between sufficient strength to retain the introducer sheath while providing atraumatic contact with the vessel wall.

The need therefore exists for an atraumatic introducer sheath which has greater retention capabilities, to thereby minimize the chances of dislodgement. By minimizing the likelihood of dislodgement, the foregoing risks to the patient would advantageously be eliminated.

SUMMARY

The present invention overcomes the disadvantages and deficiencies of the prior introducer sheaths by advantageously providing an introducer sheath having a retainer that is selectively extendable with respect to the sheath, thereby functioning to retain the sheath within the vessel. Extending the retainer radially from the introducer sheath creates an enlarged diameter region greater than the diameter of the incision into the vessel to prevent withdrawal of the sheath through the incision, and in smaller vessels, enabling the retainer to frictionally engage the vessel wall to restrict sliding movement of the sheath.

More specifically, the present invention provides a surgical vascular introducer sheath comprising first and second members and a retainer. The first member has a first longitudinally extending lumen configured and dimensioned to receive a surgical instrument therethrough and a first side opening in an outer wall in fluid communication with the first lumen. The second member has a second longitudinally extending lumen configured and dimensioned to receive the first member and a second side opening in the outer wall in fluid communication with the second lumen. The retainer is positioned at a distal portion of the first member and is movable from a first retracted position to a second extended position to limit proximal movement of the introducer. Preferably, rotational movement of the first member in a first direction moves the retainer to the extended position and rotational movement in a second direction moves the retainer to a retracted position and moves the first and second side openings from a non-aligned position to an aligned position.

Preferably, the retainer comprises a flap having a curved configuration in the extended position and an opening to allow blood flow therethrough.

The introducer sheath may further comprise a locking mechanism for maintaining the retainer in the extended position. The locking mechanism may comprise a locking pin slidable within a locking groove having a narrowed section to retain the pin. Preferably, a proximal portion of the first and second members is positioned within a housing with the locking groove positioned on the housing and the locking pin extending from the first member. The housing may further have an internal keyway slot to receive a key extending from the second member to prevent rotation of the second member.

The introducer sheath may include a second retainer movable in response to rotation of the first member between retracted and extended positions to limit proximal movement of the introducer sheath.

The present invention also provides a surgical sheath for providing a passageway for instrumentation into a vessel comprising a first tubular member having a first lumen extending longitudinally therein configured and dimensioned for receiving surgical vascular instruments therethrough, a second tubular member having a second longitudinally extending lumen wherein at least a portion of the first tubular member is positioned within the second lumen of the second tubular member, and a retainer extendable from the first tubular member. The retainer is spaced proximally from a distalmost tip of the first tubular member and limits proximal movement of the sheath with respect to the vessel to prevent dislodgement of the sheath from the vessel incision. The retainer is movable from a first position to a second position extending laterally with respect to the tubular member in response to rotational movement of the first member.

The retainer preferably comprises a flap having a curved configuration in the extended position, with the flap extending longitudinally alongside the sheath. The flap preferably comprises a spring-like member movable to the second position in response to rotational movement of the first member, with the second member having an opening to allow movement of the spring-like member to the second position.

The present invention also provides a method for preventing dislodgement of a vascular introducer sheath through a vascular incision when the introducer sheath is positioned through the incision with a distal portion extending into the vessel, the method comprising the steps of:

inserting an introducer sheath through an incision in the vessel wall so a distal portion of the sheath extends into the vessel, rotating an inner tubular member of the introducer sheath to move a retainer from a retracted position to an extended position so the retainer extends radially outwardly with respect to the introducer sheath, introducing a surgical vascular instrument into the introducer sheath;

performing a surgical step in a vascular procedure with the surgical instrument;

withdrawing the surgical instrument, the retainer preventing proximal movement of the introducer sheath through the vessel incision during withdrawal of the surgical instrument; and rotating the inner tubular member of the introducer sheath to return the retainer to its retracted position; and removing the introducer sheath from the vessel through the vascular incision.

The step of rotating the inner tube of the introducer sheath to move the retainer from the retracted position to the extended position preferably aligns holes in the introducer sheath to allow blood flow for therethrough.

BRIEF DESCRIPTION OF THE DRAWINGS

Preferred embodiment(s) of the present disclosure are described herein with reference to the drawings wherein:

FIG. 1 is a perspective view of a first embodiment of the introducer sheath of the present invention with the retainer in the retracted position;

FIG. 2 is a perspective view of the introducer sheath of FIG. 1 with the retainer in the extended position;

FIG. 3 is a longitudinal cross-sectional view of the introducer sheath of FIG. 1 with the retainer in the extended position;

FIG. 4 is a transverse cross-sectional view taken along lines 4—4 of FIG. 3;

FIG. 5 is an exploded view of the introducer sheath of FIG. 1;

FIG. 6 is a transverse cross-sectional view showing the orientation of the side port and keyway of the housing;

FIG. 7 is a transverse cross-sectional view showing the dialysis holes of the inner and outer tubular members out of alignment prior to deployment of the retainer;

FIG. 8 is a perspective view of the introducer sheath of FIG. 1 showing the components in phantom inside the housing;

FIG. 9 is an enlarged view of the locking pin and groove of FIG. 8;

FIG. 10 is a perspective view of the distal portion of an alternate embodiment of the introducer sheath having an angled tip to facilitate insertion;

FIG. 11 is a side view of the introducer sheath of FIG. 10;

FIG. 12 illustrates the introducer sheath of FIG. 1 inside a vessel with the retainer in the extended position to prevent withdrawal of the introducer sheath through the incision;

FIG. 13 illustrates the distal portion of the introducer sheath of FIG. 1 inserted into a small vessel wherein the retainer, in its extended position, frictionally engages the vessel wall to limit proximal movement of the introducer sheath;

FIG. 14 illustrates a catheter being withdrawn from the introducer sheath of FIG. 1, the retainer engaging the vessel wall to limit proximal movement;

FIG. 15 is a perspective view of the distal portion of another alternate embodiment of the introducer sheath of the present invention having two retainers extending from the inner tubular member;

FIG. 16 is a perspective view of a distal portion of yet another alternate embodiment of the introducer sheath of the present invention having a retainer deployable by longitudinal movement of the inner tubular member; and FIG. 17 is perspective view of the distal portion of the introducer sheath of FIG. 16 showing the retainer in the extended position.

DETAILED DESCRIPTION OF PREFERRED EMBODIMENTS

Introducer sheaths are commonly used in vascular surgery to provide a passageway for instrumentation. The introducer sheath is inserted into a vessel or a graft (e.g. a dialysis graft) and a variety of instruments for performing the specific surgical procedure are introduced therethrough to access the surgical site. Since the instruments are repeatedly inserted and withdrawn during the surgical procedure, and have a diameter closely matching the internal diameter of the sheath, the introducer sheath has the tendency to be dislodged, and perhaps even withdrawn from the vessel incision as discussed above. Additionally, certain instruments, such as balloon catheters, may have a larger diameter during withdrawal then insertion, thereby increasing the chances of dislodgment. The introducer sheaths of the present invention advantageously have a retainer for limiting proximal movement and preventing full dislodgement of the introducer sheath during surgery. That is, the retainer is extendable from the sheath to create an enlarged diameter or circumferential portion exceeding the size of the vessel incision and in smaller vessels, frictionally engaging the vessel wall.

Referring now in detail to the drawings where like reference numerals identify similar or like components throughout the several views, FIGS. 1–9 illustrate a first embodiment of the introducer sheath of the present invention, designated generally by reference numeral 10.

The introducer sheath 10 has a proximal portion 12, a distal portion 14, an outer tubular member 20 and an inner tubular member 30 disposed concentrically within the outer tubular member 20. A retainer 40, in the form of a flap, extends from inner tube 30. Retainer 40 is movable from a retracted position where it is retained by outer tube 20, to an extended (blocking) position where it extends radially outwardly from the inner tube 30 and outer tube 20 as shown in FIG. 2. This radial movement increases the overall circumference or diameter of the introducer sheath 10, thereby causing the sheath 10 to engage vessel wall or wall surrounding the incision in the manner described below.

Outer tube 20, preferably circular in cross section as shown, (although oval or other shapes can be utilized) has a distal portion 21, a proximal portion 23 and a central longitudinal lumen 22 dimensioned and configured to receive inner tube 30. A cutout 25 in the outer tube 20 is configured to allow passage of flap 40, which preferably extends integrally from inner tube 30 and longitudinally alongside the tube ("l") in the extended position. Distal nose 28 of tube 20 is slightly tapered to facilitate insertion through the incision and vessel.

Inner tube 30 is also preferably circular in cross section (although oval or other shapes can be utilized and has a distal portion 31 and a proximal portion 33. Central lumen 32 extends longitudinally along the entire length of the inner tube 30 and is configured and dimensioned to receive surgical instruments therethrough.

Retainer or flap 40 is deployed by rotation of inner tube 30. Flap 40 is preferably curved and U-shaped as shown to form an opening 43 to allow blood flow therethrough. The smooth shaped surface provides atraumatic contact with the vessel wall. In the retracted position, retainer 40 is out of alignment with cutout 25 of outer tube 20. Thus, the inner wall of the outer tube 20 maintains the retainer 40 in the retracted position. To deploy the retainer 40, inner tube 30 is rotated in the direction of the arrow to align the retainer 40 with the cutout or opening 25, thereby allowing the retainer 40 to move to an extended position to function to block proximal movement of the introducer sheath 10.

Retainer 40 is preferably composed of a spring-like material biased to the extended position so that it will more easily move to its extended position when aligned with cutout 25 in outer tube 20. An edge 41 of the outer wall adjacent the cutout can be angled to facilitate return of the spring-like retainer to the retracted position when the inner tube 30 is rotated in the reverse direction.

With reference to FIGS. 5, 8 and 9, introducer sheath 10 further includes a retainer locking element to maintain the retainer or flap 40 in the extended position. Inner tube 30 has a locking pin 85 extending from enlarged head 86 which is received within transverse locking groove 90 of housing 92. As shown in FIGS. 8 and 9, locking groove 90 is slightly arcuate and has two lobes 94, 96 at opposite ends and adjacent narrowed regions 93, 95. When the retainer 40 is in the retracted position of FIG. 1, locking pin 85 is seated within lobe 96 and is prevented from movement within the groove 90 by narrowed region 95. To move the retainer to the extended position to limit movement of the introducer sheath 10, locking pin 85 is grasped by the user and moved within groove 90. By supplying sufficient force, locking pin 85 is forced through narrowed region 95, slightly stretching the flexible material around the groove. Movement of locking pin 85 rotates the inner tube 30, while the outer tube 20 remains stationary, thereby moving retainer 40 to its extended position. This pin and groove arrangement also keeps inner tube 30 fixed longitudinally during rotation.

To lock the retainer 40 in its extended position, locking pin 85 is forced through narrowed region 93 into lobe 94. After being slightly stretched by passage of locking pin 85, narrowed region 93 returns to its original configuration to block exit of locking pin 85. Thus, locking pin 85 is prevented from sliding within locking groove 90, thereby blocking inner tube 30 from rotation and maintaining retainer 40 in the blocking (extended) position.

When it is desired to move retainer 40 back to its retracted position, locking pin 85 is forced through narrowed regions 93 and 95, by movement in the reverse direction, and returned to lobe 96. During movement of the inner tube 30 in either direction, outer tube 20 remains stationary due to the engagement of key 75 of enlarged head 77 with keyway slot 91 of housing 92, shown in phantom in FIG. 5. Inner tube 30 is prevented from sliding longitudinally by groove 90. As an alternative to the keyway, an adhesive or any energy welding system, e.g. radiofrequency, ultrasonic, etc., can be utilized to keep the outer tube 20 stationary.

Visual indicators could optionally be provided at the lobes to indicate to the user the position of the retainer. For example, an "R" for retracted can be provided adjacent lobe 96 on the housing 92 and an "E" for extended can be provided adjacent lobe 94.

With continued reference to FIG. 5, housing 92 has assembly slot 99 communicating with groove 90 for ease of assembly. That is, for assembly, locking pin 95 is slid through slot 99 into groove 90 and locking cap 100 is placed over distal portion 98 of housing 92 effectively closing slot 99 to lock pin 85 within groove 90. A valve 102 is positioned within housing 92 to prevent outflow of blood through proximal opening 107 of housing 92. If introducer sheath 10 is used for dialysis as explained below, the valve is preferably a silicone valve to accommodate additional pressure from the vacuum for blood withdrawal. A donut like element 104, preferably composed of foam and having central opening 105, is positioned between valve 102 and proximal wall 97 of housing 92. Donut 104 is preferably laced with a lubricant such as silicone to promote lubricity during insertion of surgical instruments and to prevent valve damage due to friction.

The introducer sheath 10 includes a plurality of holes for either blood withdrawal or blood return so the introducer sheath can remain in the body for dialysis or other surgical procedures. As shown in FIGS. 5 and 7, outer tube 20 has side holes 61 formed through its outer wall 64 and inner tube 30 has side holes 71 formed through outer wall 74. These holes 61, 71, when aligned, allow for passage of blood through lumen 72, out through side aperture 79 in enlarged head portion 77, and exiting through side port 109 in housing 92. Conventional tubing 110, as shown in FIG. 1, is connected to side port 109. Tubing 110 includes conventional tube clamp 112 and luer fitting 114 which do not form part of this invention and are therefore not further described. If used for dialysis, two introducer sheaths 10 could be provided: one sheath 10 for withdrawal of blood from the vessel for passage to the dialysis machine and a second sheath 10 for return of blood from the dialysis machine to the vessel. Alternatively, if used for dialysis, introducer sheath 10 could be use for blood withdrawal or delivery, and another instrument, such as dialysis needle could be used for opposite blood flow. Also, although three holes are shown spaced approximately 120 degrees apart, it should be appreciated that other spacings and fewer or a greater number of holes could be provided for dialysis or for other procedures.

FIG. 7 illustrates the interaction of the side holes 61 and 71 of the outer and inner tubes 20, 30 respectively. When the retainer 40 is in the retracted position, holes 61 and 71 are out of alignment as shown, thereby preventing blood flow through central lumen 32. However, when inner tube 30 is rotated to extend retainer 40 to the blocking (extended) position, side holes 61 are rotated into alignment with side holes 71. Thus when inner tube 30 is locked in the rotated position with locking pin 85 retained in lobe 94, holes 61 and 71 are in alignment and blood can pass through these holes into central lumen 32.

Proximal opening 107 in housing 92 allows for passage of a guidewire and surgical instrumentation, the guidewire and surgical instruments passing through opening 105 in donut 104, through valve 102 and through opening 106 in cap 100 into central lumen 32.

FIGS. 10 and 11 illustrate an alternate embodiment of the introducer sheath having an angled or beveled end to facilitate insertion. Introducer sheath 50 has tip 52 at an angle greater than 90 degrees as shown so that edge 54 will enter the tissue before edge 56 to reduce the penetration force. This angled tip can be provided on any of the introducer sheaths described herein.

FIG. 15 illustrates an alternate embodiment wherein locking sheath 120 is provided with two retainers 122, spaced apart as shown. Locking sheath 120 is substantially identical to the locking sheath of FIG. 1, in all other respects. Each retainer 122 is attached to inner tube 126, extends through a cutout 123 in outer tube 125, and is identical to retainer 40 of FIG. 1. The retainers 122 are shown in their retracted position, and are deployed simultaneously to their U-shaped configurations upon rotation of the inner tube 126 as described above with respect to the embodiment of FIGS. 1–9. Holes 129 are provided for blood flow for dialysis.

FIGS. 16 and 17 illustrate another alternate embodiment of the introducer sheath of the present invention. Outer tube 202 of introducer sheath 200 has an integrally formed retainer flap 205. Upon longitudinal movement of inner tube 207, i.e. proximal movement in the direction of the arrow, flap 205, attached to inner tube 207 at edge 209 is forced to a raised (extended) position, forming a V-shaped retaining element. This laterally extending flap functions to prevent dislodgement of the introducer sheath 200 during withdrawal of surgical instrumentation through lumen 204 in a similar manner as the other aforedescribed retainer embodiments. An opening 206 may optionally be provided to allow passage of blood when flap 205 is deployed to the extended position.

The tips of any of the foregoing introducer sheaths can have radiopaque markers to provide visual indication of the catheter tip location. The markers can take a variety of forms such as a circular marker band wrapped around the outer tube or a radiopaque material welded onto the tip.

The interior of the inner tubes of any of the foregoing embodiments can have a hydrophilic coating to facilitate instrument insertion through its lumen by reducing frictional contact. The outer surface of the outer tube could also be provided with a hydrophilic coating to reduce frictional contact with the skin and vessel during insertion FIGS. 12–14 illustrate the introducer sheath of the present invention in use. The introducer sheath 10 of FIGS. 1–9 is illustrated and described, (with the tubing removed for clarity) it being understood however, that any of the aforedescribed introducer sheaths would be utilized in a similar manner.

FIG. 12 illustrates introducer sheath 10 positioned inside a vessel "v", such as a common femoral artery. Sheath 10 is inserted through incision "i" in the vessel wall to gain access to the interior of the vessel. Once positioned as shown, the inner tube is rotated to deploy retainer 40 to an extended position as shown. In this extended position, the sheath 10 cannot fit through the incision "i". Consequently when surgical instruments such as a balloon catheter shown in FIG. 14 are inserted and then withdrawn, the retainer 40 will contact the vessel wall around the incision, preventing undesirable withdrawal of the introducer sheath 10 through the incision. Being retained or "locked" inside the vessel, various instruments can be inserted and withdrawn through the sheath lumen without the introducer sheath 10 becoming dislodged and causing the problems associated with such dislodgement discussed above. The pin and groove locking arrangement maintains the retainer 40 in the extended (blocking) position as desired.

When the introducer sheath 10 is ready to be removed from the vessel "v", the inner tube is rotated in the reverse direction, disengaging the pin and groove locking arrangement, to thereby return the retainer to its retracted position substantially flush with the outer surface of the outer tube. Thus, the introducer sheath 10 can be withdrawn through incision "i".

When used in smaller vessels, not only will the retainer 40 of the introducer sheath 10 prevent full withdrawal from the incision, but it will contact the vessel wall "u" downstream of the incision as shown in FIG. 13. This contact results in frictional engagement with the wall, thereby restricting unwanted proximal movement of the introducer sheath 10 during withdrawal of surgical instruments, such as the balloon catheter of FIG. 14. The curved surface 41 of flap 40 provides atraumatic contact with the vessel wall.

Although the introducer sheath is preferably composed of Pebax material, other materials such as nylon, polyethyelene, or polypropylene, or composites with braided components, can be utilized While the above description contains many specifics, those specifics should not be construed as limitations on the scope of the disclosure, but merely as exemplifications of preferred embodiments thereof. For example, the introducer sheaths could also be slightly curved or bendable/shapeable. Those skilled in the art will envision many other possible variations that are within the scope and spirit of the disclosure as defined by the claims appended hereto.

What is claimed is:

1. A method for preventing dislodgement of a vascular introducer sheath through a vascular incision when the introducer sheath is positioned through the incision with a distal portion extending into the vessel, the method comprising the steps of:

inserting an introducer sheath through the incision in the vessel wall so the distal portion of the sheath extends into the vessel, the sheath having a cutout formed therein;

rotating an inner tubular member of the introducer sheath to move a retainer into alignment with the cutout to enable the retainer to move from a refracted position to an extended position so the retainer extends radially outwardly with respect to the introducer sheath;

introducing a surgical vascular instrument into the introducer sheath;

performing a surgical step in a vascular procedure with the surgical instrument;

withdrawing the surgical instrument, the retainer preventing proximal movement of the introducer sheath through the vessel incision during withdrawal of the surgical instrument; and rotating the inner tubular member of the introducer sheath to return the retainer to retracted position, the step of rotating moving the retainer out of alignment with the cutout; and removing the introducer sheath from the vessel through the vascular incision.

2. The method of claim 1, wherein the step of rotating the inner tubular member of the introducer sheath to move the retainer from the retracted position to the extended position aligns holes in the introducer sheath to allow blood flow therethrough for dialysis.

3. The method of claim 2, further comprising the step of locking the retainer in the extended position.

4. The method of claim 3, wherein the step of locking the retainer in the extended position includes the step of sliding a member within a locking groove and into a locking region of the groove.

5. The method of claim 4, wherein the step of rotating the inner tube to move the retainer to the extended position enables blood flow through an opening in the retainer.

6. The method of claim 1, wherein the step of rotating the inner tubular member further moves a second retainer from a retracted to an extended position.

7. The method of claim 1, wherein the step of rotating the inner tube to move the retainer to extend position enables blood flow through an opening in the retainer.

8. The method of claim 1, wherein an outer tube of the introducer sheath remains stationary during the step of rotating the inner tubular member.

9. A method for preventing dislodgement of a vascular introducer sheath through a vascular incision when the introducer sheath is positioned through the incision with a distal portion extending into the vessel, the method comprising the steps of:

providing an introducer sheath;

inserting the introducer sheath through the incision in the vessel wall so the distal portion of the sheath extends into the vessel;

grasping a mechanism of the introducer sheath and moving the mechanism to move an inner tubular member of the introducer sheath to thereby move a retainer from a first position to a second position so the retainer aligns with a cutout and extends radially outwardly with respect to the introducer sheath, the grasping mechanism also locking the retainer in the second position;

introducing a surgical vascular instrument through the introducer sheath;

performing a surgical step in a vascular procedure with the surgical instrument;

withdrawing the surgical instrument, the retainer in the second position preventing proximal movement of the introducer sheath through the vessel incision during withdrawal of the surgical instrument;

grasping and moving the mechanism of the introducer sheath to move the inner tubular member of the introducer sheath to return the retainer to the first position; and removing the introducer sheath from the vessel through the vascular incision.

10. The method of claim 9, wherein the step of moving the grasping mechanism to lock the retainer in the second position moves a pin into locking engagement with a groove.

11. The method of claim 9, wherein the step of moving the inner tubular member to move the retainer comprises the step of moving the inner tubular member longitudinally.

12. The method of claim 11, wherein the grasping mechanism further locks the retainer in the second position.

13. The method of claim 9, wherein the step of moving the inner tube to move the retainer to the extended position enables blood flow through an opening in the retainer.

14. The method of claim 9, wherein the step of moving the inner tubular member to move the retainer to the second position comprises the step of moving the inner tubular member in a first rotational direction.

15. A method for preventing dislodgement of a vascular introducer sheath through a vascular incision when the introducer sheath is positioned through the incision with a distal portion extending into the vessel, the method comprising the steps of:

providing an introducer sheath having an inner tubular member having a flap with first and second spaced apart edges extending from the inner tubular member;

inserting the introducer sheath through an incision in the vessel wall so a distal portion of the sheath extends into the vessel;

moving an inner tubular member of the introducer sheath to move the flap from a first position to a second position so the flap extends radially outwardly with respect to the introducer sheath to expose an arcuate surface extending transverse to a longitudinal axis of the introducer sheath and to allow blood flow along a longitudinal axis thereof;

introducing a surgical vascular instrument through the introducer sheath;

performing a surgical step in a vascular procedure with the surgical instrument;

withdrawing the surgical instrument, the flap in the second position preventing proximal movement of the introducer sheath through the vessel incision during withdrawal of the surgical instrument;

moving the inner tubular member of the introducer sheath to return the flap to its first position; and removing the introducer sheath from the vessel through the vascular incision.

16. A method for preventing dislodgement of a vascular introducer sheath through a vascular incision when the introducer sheath is positioned through the incision with a distal portion extending into the vessel, the method comprising the steps of:

providing an introducer sheath having an inner tubular member having a flap with an opening longitudinally aligned with a longitudinal axis of the introducer sheath to enable blood flow therethrough along a longitudinal axis;

inserting the introducer sheath through an incision in the vessel wall so a distal portion of the sheath extends into the vessel;

moving an inner tubular member of the introducer sheath to move the retainer from a first position to a second position so the retainer extends radially outwardly with respect to the introducer sheath and the opening in the retainer allows blood flow therethrough;

introducing a surgical vascular instrument through the introducer sheath;

performing a surgical step in a vascular procedure with the surgical instrument;

withdrawing the surgical instrument, the flap in the second position preventing proximal movement of the introducer sheath through the vessel incision during withdrawal of the surgical instrument;

moving the inner tubular member of the introducer sheath to return the retainer to its first position; and removing the introducer sheath from the vessel through the vascular incision.

* * * * *